United States Patent [19]

Zolninger

[11] Patent Number: 5,485,357
[45] Date of Patent: Jan. 16, 1996

[54] FLASHLIGHT WITH MOUTH SUPPORT AND ASSOCIATED CONTROLS

[76] Inventor: Gregory C. Zolninger, 7128 Hull Rd., Cherryville, N.C. 28021

[21] Appl. No.: 269,144

[22] Filed: Jun. 30, 1994

[51] Int. Cl.⁶ .................................................. F21L 15/08
[52] U.S. Cl. ........................ 362/103; 362/190; 362/205; D26/39
[58] Field of Search ................................... 362/103, 108, 362/190, 191, 205; D26/39; 623/24; 128/77

[56] References Cited

U.S. PATENT DOCUMENTS

| D. 302,334 | 7/1989 | DeGuevara | D26/39 |
|---|---|---|---|
| D. 332,500 | 1/1993 | Churchill | D26/46 |
| 2,299,467 | 10/1942 | Colby | 362/191 |
| 3,225,982 | 12/1965 | Melton | 362/108 |
| 3,710,092 | 1/1973 | Olbermann, Jr. | 362/205 |
| 3,795,281 | 3/1974 | Cloran | 623/24 |
| 4,533,982 | 8/1985 | Kozar | 362/190 |
| 4,728,812 | 3/1988 | Sheriff et al. | 128/777 |
| 4,794,496 | 12/1988 | Lanes et al. | 362/103 |
| 4,967,323 | 10/1990 | Johnson et al. | 362/103 |
| 5,034,862 | 7/1991 | Liston | 362/191 |
| 5,063,483 | 11/1991 | Feilmeier et al. | 362/190 |
| 5,144,546 | 9/1992 | Burdi | 362/191 |
| 5,184,884 | 2/1993 | Maglica et al. | 362/191 |
| 5,226,712 | 7/1993 | Lucas | 362/190 |

*Primary Examiner*—Ira S. Lazarus
*Assistant Examiner*—Sara Sachie Raab

[57] ABSTRACT

A flashlight with mouth support and associated controls comprising: a flashlight having a forward end with a bulb, a rearward end with a separable cap with a spherical recess and an intermediate cylindrical extent therebetween; a mouthpiece fabricated of an elastomeric material with an arcuate inner surface adapted to be supported by the teeth of a user and an enlarged external surface positionable between the teeth and lips of the user and a central post extending forwardly thereof; and electrical coupling components between the mouthpiece and the flashlight including a central axial aperture extending from the flashlight to the cap and to an intermediate section of the mouthpiece with electrical wires extending therethrough.

1 Claim, 5 Drawing Sheets

FLASHLIGHT WITH MOUTH SUPPORT AND ASSOCIATED CONTROLS

BACKGROUND OF THE INVENTION

1. Field of the Invention

The present invention relates to a flashlight with mouth support and associated controls and more particularly pertains to supporting a flashlight by the mouth of the user and controlling its operation by the users mouth.

2. Description of the Prior Art

The use of flashlights of various designs having a wide variety of supports and controls is known in the prior art. More specifically, various designs having a wide variety of supports and controls heretofore devised and utilized for the purpose of supporting a flashlight while working in dark or dimly lit areas, the support and control of the flashlight being done by a large number of techniques are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 5,184,884 to Maglica a flashlight holder clamp assembly.

U.S. Pat. No. 5,144,546 to Burdi discloses a flashlight holder.

U.S. Pat. No. 5 034 862 to Liston discloses a multiposition flashlight holder.

U.S. Pat. No. 3,710,092 to Olbermann, Jr. discloses a flashlight with accessory holder.

U.S. Pat. No. Des.332,500 to Churchill discloses the design of a mouth supported flashlight.

In this respect, the flashlight with mouth support and associated controls according to the present invention substantially departs from the conventional concepts and designs of the prior art, and in doing so provides an apparatus primarily developed for the purpose of supporting a flashlight by the mouth of the user and controlling its operation by the users mouth.

Therefore, it can be appreciated that there exists a continuing need for new and improved flashlight with mouth support and associated controls which can be used for supporting a flashlight by the mouth of the user and controlling its operation by the users mouth. In this regard, the present invention substantially fulfills this need.

SUMMARY OF THE INVENTION

In view of the foregoing disadvantages inherent in the known types of various designs having a wide variety of supports and controls now present in the prior art, the present invention provides an improved flashlight with mouth support and associated controls. As such, the general purpose of the present invention, which will be described subsequently in greater detail, is to provide a new and improved flashlight with mouth support and associated controls and method which has all the advantages of the prior art and none of the disadvantages.

To attain this, the present invention essentially comprises a flashlight with mouth support and associated controls comprising, in combination: a flashlight having a forward end with a bulb, a rearward end with a separable cap with a spherical recess and an intermediate cylindrical extent therebetween; a mouthpiece fabricated of an elastomeric material with an arcuate inner surface adapted to be supported by the teeth of a user and an enlarger external surface positionable between the teeth and lips of the user and a central post extending forwardly thereof, the forward post terminating in a ball adapted to be received in the correspondingly sized and shaped recess in the cap for allowing rotational movement of the cap and flashlight with respect to the mouthpiece; electrical coupling components between the mouthpiece and the flashlight including a central axial aperture extending from the flashlight to the cap and to an intermediate section of the mouthpiece with electrical wires extending therethrough; and a contact switch located within the central extent of the mouthpiece, the contact switch having electrically conductive plates normally out of contact but positionable into contact with each other to close the circuit and light the bulb.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved flashlight with mouth support and associated controls which have all the advantages of the prior art various designs having a wide variety of supports and controls and none of the disadvantages.

It is another object of the present invention to provide a new and improved flashlight with mouth support and associated controls which may be easily and efficiently manufactured and marketed.

It is further object of the present invention to provide a new and improved flashlight with mouth support and associated controls which are of durable and reliable constructions.

An even further object of the present invention is to provide a new and improved flashlight with mouth support and associated controls which are susceptible of a low cost of manufacture with regard to both materials and labor, and which accordingly are then susceptible of low prices of sale to the consuming public, thereby making such flashlight with mouth support and associated controls economically available to the buying public.

Still yet another object of the present invention is to provide a new and improved flashlight with mouth support and associated controls which provide in the apparatuses and methods of the prior art some of the advantages thereof, while simultaneously overcoming some of the disadvantages normally associated therewith.

Still another object of the present invention is to support a flashlight by the mouth of the user and control its operation by the users mouth.

Lastly, it is an object of the present invention to provide a new and improved flashlight with mouth support and associated controls comprising: a flashlight having a forward end with a bulb, a rearward end with a separable cap with a spherical recess and an intermediate cylindrical extent therebetween; a mouthpiece fabricated of an elastomeric material with an arcuate inner surface adapted to be supported by the teeth of a user and an enlarger external surface positionable between the teeth and lips of the user and a central post extending forwardly thereof; and electrical coupling components between the mouthpiece and the flashlight including a central axial aperture extending from the flashlight to the cap and to an intermediate section of the mouthpiece with electrical wires extending therethrough.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
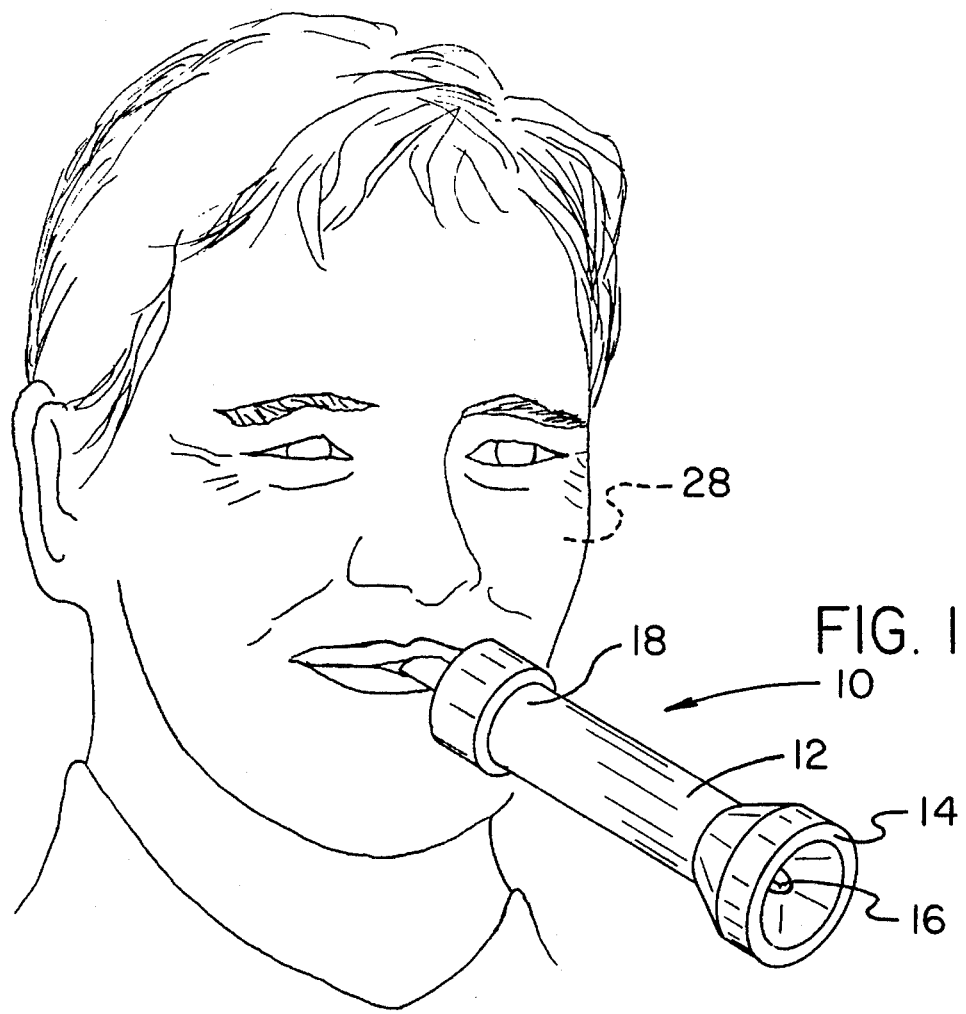
FIG. 1 is a perspective view of the preferred embodiment of the flashlight with mouth support and associated controls constructed in accordance with the principles of the present invention.
Figure 2:
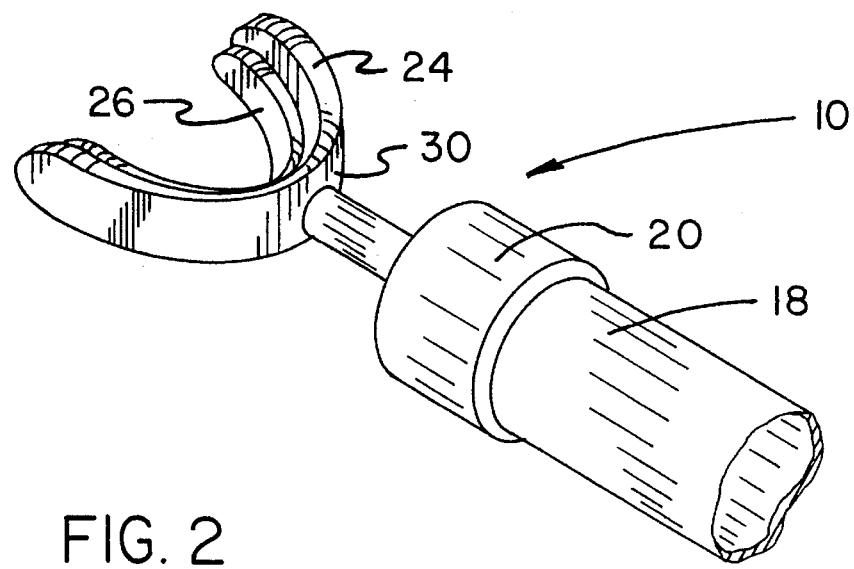
FIG. 2 is a perspective view of the interior end of the flashlight assembly shown in FIG. 1.
Figure 3:
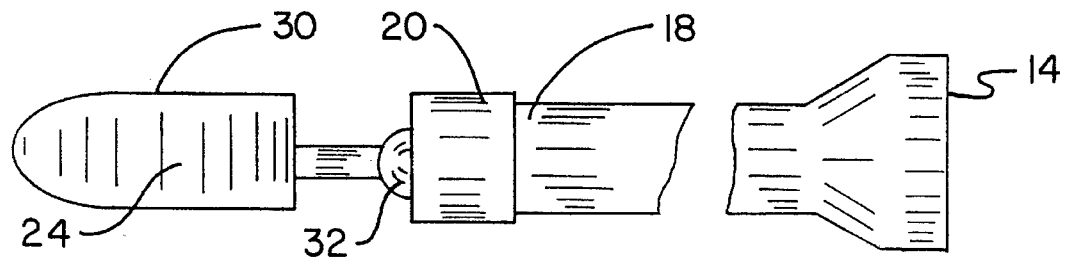
FIG. 3 is a side elevational view of the flashlight assembly of the prior Figure.
Figure 4:
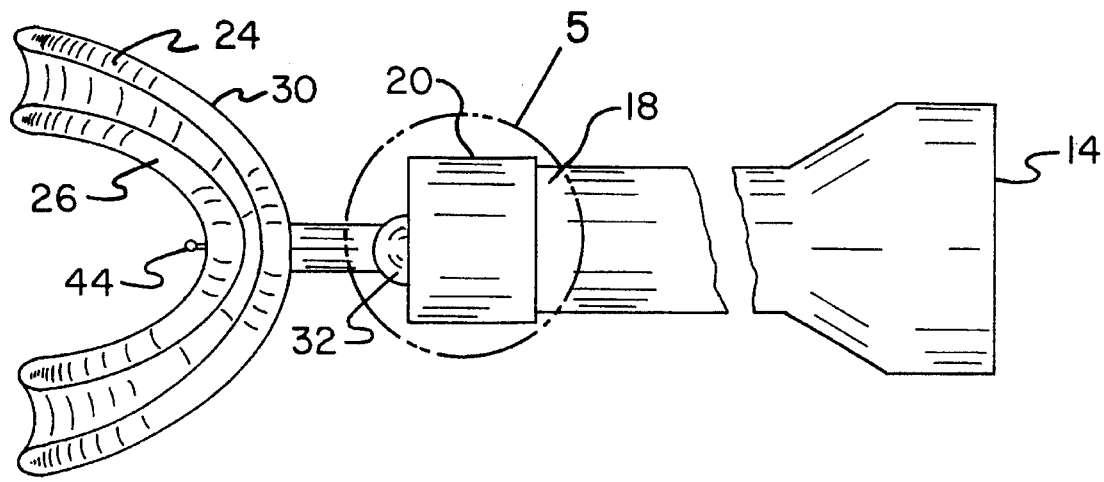
FIG. 4 is a top elevational view of the flashlight assembly of the prior Figure.

With reference now to the drawings, and in particular to FIG. 1 thereof, the preferred embodiment of the new and improved flashlight with mouth support and associated controls embodying the principles and concepts of the present invention and generally designated by the reference numeral 10 will be described.

The invention, the new and improved flashlight with mouth support and associated controls is comprised of a plurality of components. In their broadest context, such components include a flashlight, a mouthpiece, electrical coupling components and a switch. Such components are specifically configured and correlated with respect to each other so as to attain the desired objective.

More particularly, in the invention of the present application, the invention is in a system 10 having as one of its central components, a flashlight 12. The flashlight has a forward end 14. The forward end has a bulb 16. The flashlight also has a rearward end 18. The rearward end has a separable cap 20 with a centrally located spherical recess at its innermost end. The flashlight also has an intermediate cylindrical extent therebetween which normally houses the batteries for powering the bulb.

The other major component of the system 10 which can be readily seen is a mouthpiece 24. The mouthpiece is fabricated of an elastomeric material. It has an arcuate inner surface 26. Such surface is adapted to be supported by the teeth of a user 28. The mouthpiece has an enlarged external surface 30 positionable between the teeth and lips of a user. The mouthpiece also has a central post 32 extending forwardly thereof. The forwardly extending post terminates in a ball 32. The ball is adapted to be received in the recess of the cap which is sized and shaped to correspond to the recess of the flashlight. The relationship between the ball and recess is such as to allow for rotational movement of the cap and flashlight with respect to the mouthpiece.

Next provided is the electrical coupling components 36 between the mouthpiece and the flashlight. Such coupling components include a central axial aperture 38. Such aperture extends from the flashlight to the cap and to an intermediate section of the mouthpiece. Electrical wires 40 extend through the aperture.

Figure 9:
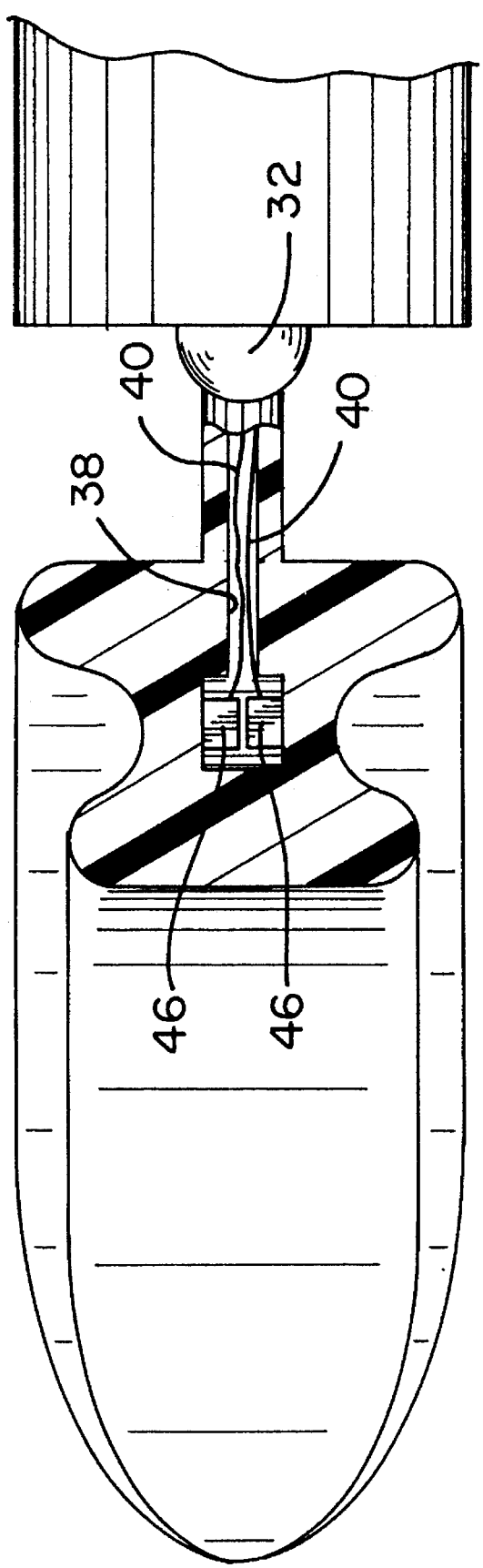
FIG. 9 is a cross sectional view similar to FIG. 7 but illustrating an alternate embodiment of the invention.

Next provided in the system 10 is a contact switch 44. The contact switch is located within the central extent of the mouthpiece. The contact switch has electrically conductive plates 46. Such plates are normally out of contact. The plates, however, may be positionable into contact with each other to close the circuit and light the bulb. Such lighting may occur without the use of the hands of a user. Pressure is applied simply by closing the teeth together over the mouthpiece. Note FIG. 9.

Figure 6:
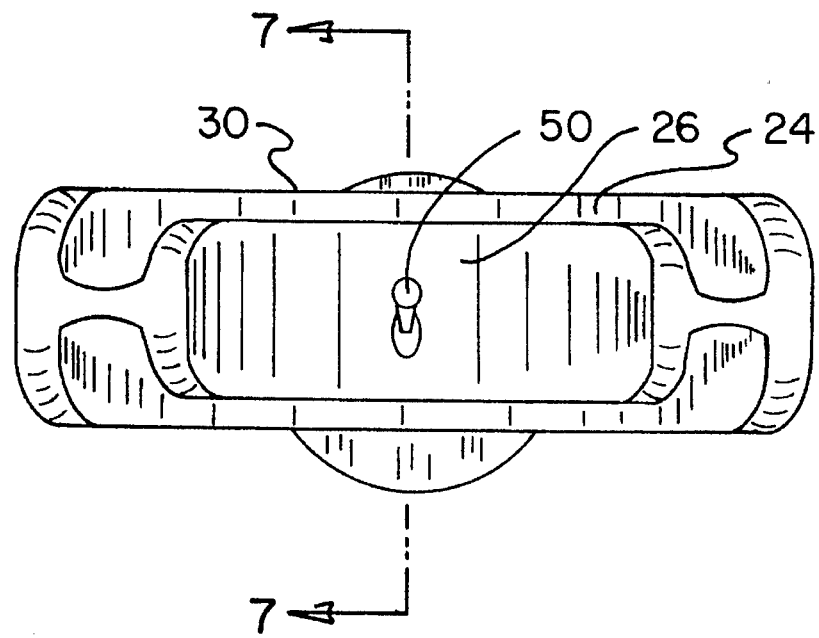
FIG. 6 is a rear elevational view of the flashlight assembly of the prior Figure.
Figure 5:
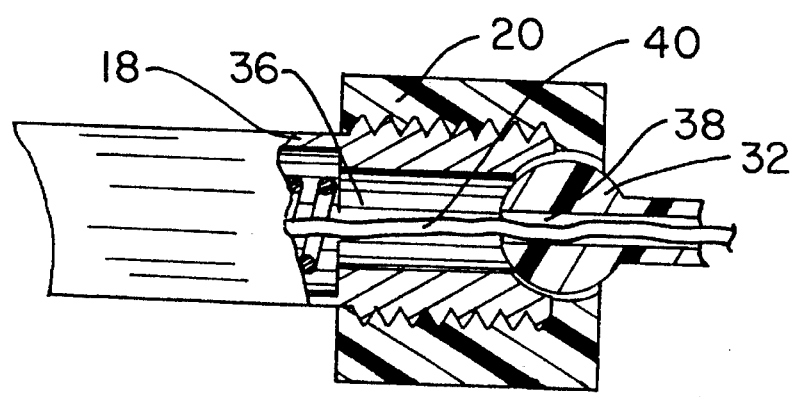
FIG. 5 is an enlarged cross sectional view of a central portion of the flashlight assembly shown in the prior figures taken about circle 5 of FIG. 4.
Figure 7:
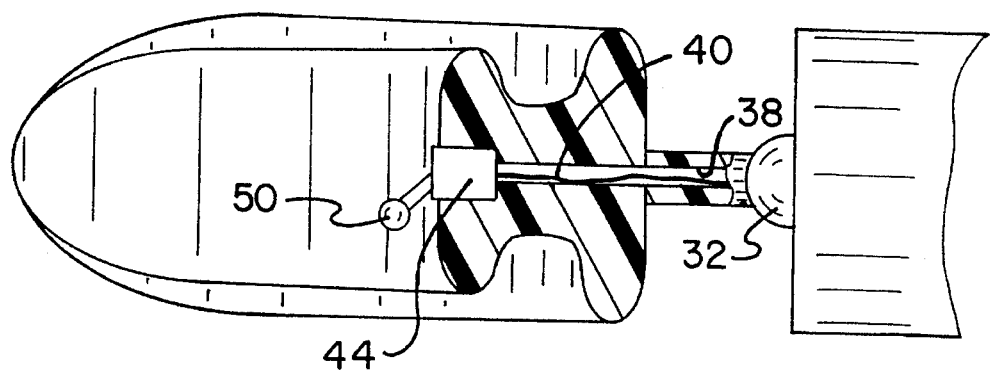
FIG. 7 is a cross sectional view taken along line 7—7 of FIG. 6.

The particular embodiment shown in FIGS. 6 and 7 is essentially the same as that described above. In such embodiment, however, a switch 50 is located at the rearward end of the wires. The switch is exposed for positioning at the central interior surface of the mouthpiece. In this manner, a user may turn the switch through the action of his tongue. When doing so, the forward ends of the wires adjacent the switch will function to make and break the circuit. In this manner the bulb is turned on and off.

Figure 8:
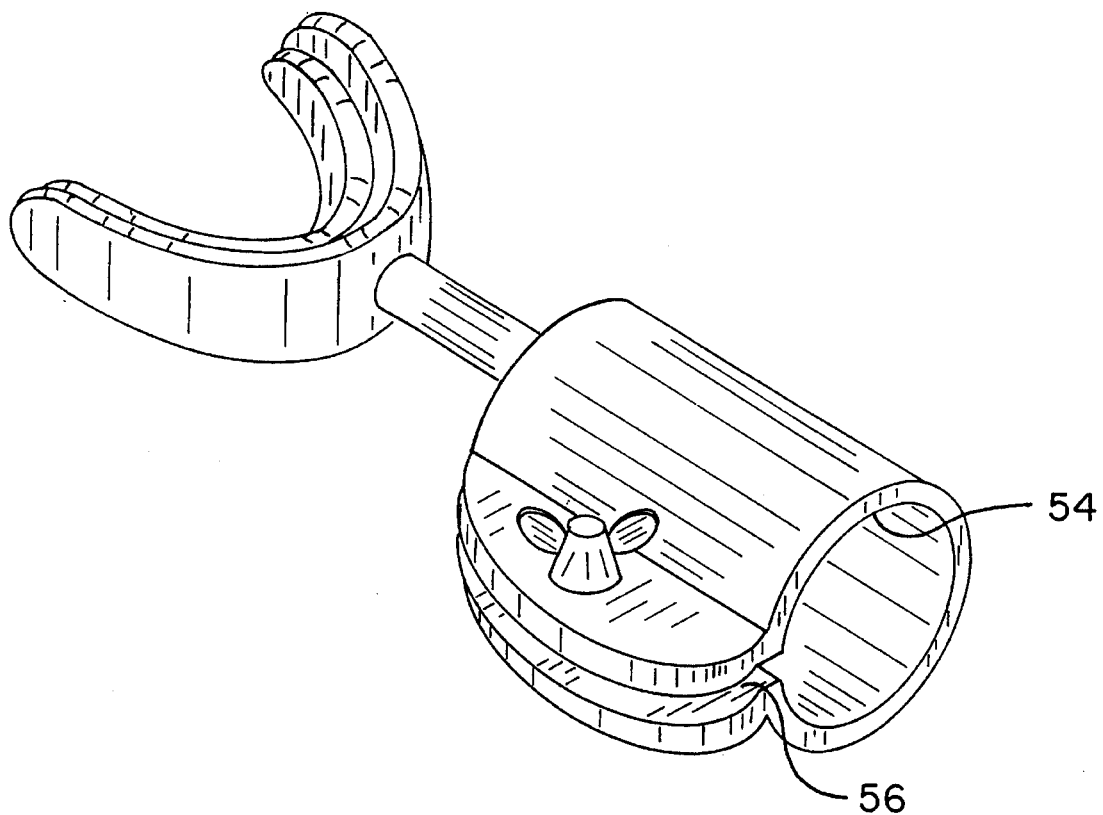
FIG. 8 is a perspective illustration of a support assembly for a flashlight in accordance with an alternate embodiment of the invention.

In the FIG. 8 embodiment of the invention, the electrical wires coupling the flashlight and switch are eliminated. In such embodiment, as readily seen in FIG. 8, a cylindrical opening 54 is formed in the forward end of the post. Such opening has an axis coextensive with the axis of the flashlight. In this manner, the opening is for receiving the rear end of the flashlight to be held. The flashlight is turned on and off in the normal fashion. A bolt and wing nut extend through an aperture in the post perpendicular to the axis along a slot 56 in the axis for enlarging or reducing the size of the opening. In this manner, the flashlight may be held tightly at the end of the post.

The present invention is a small flashlight that can be held in one's mouth. The idea, of course is to free one's hands to do the work in the area being illuminated. This is a very handy tool for homeowners, do-it-yourselfers, electricians, and especially plumbers, who frequently work in dark and hard to get at places.

The present invention is similar to any small flashlight. However, fastened to the flashlight is a U-shaped mouthpiece that extends out from its rear. This extension is about ½ to 1 inch long, permitting the user to hold a flashlight securely in their mouth while performing a variety of different tasks. The rod and mouthpiece are molded in one piece from plastic or hard rubber and is similar in design to those used by professional or amateur athletes involved in contact sports. A deluxe version could contain a switch that would turn the light on or off by simply biting down on the mouthpiece. The mouthpiece can be produced separately to be installed on existing flashlights to permit them to be used in a similar manner.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved flashlight with mouth support and associated controls, the apparatus comprising, in combination:

a flashlight having a forward end with a bulb, a rearward end with a separable cap formed with an inwardly extending spherical recess and an intermediate cylindrical extent between the forward end and rearward end, the separable cap being separable from the remainder of the flashlight;

a mouthpiece fabricated of an elastomeric material with an arcuate inner surface capable of being supported by a user's teeth an enlarged external surface capable of being positioned between the teeth and lips of the user an intermediate portion connecting the inner surface and the external surface and a central post extending forwardly thereof, the central post terminating in a ball adapted to be received within the spherical recess in the separable cap for allowing rotational movement of the cap and flashlight with respect to the mouthpiece;

electrical coupling components between the mouthpiece and the flashlight including a central axial aperture extending from the flashlight to the cap and to an intermediate section of the mouthpiece with electrical wires extending therethrough; and a contact switch located within the intermediate portion of the mouthpiece, the contact switch having electrically conductive plates normally out of contact but positionable into contact with each other to close the circuit and light the bulb.

* * * * *